United States Patent [19]

Henriques de Gatztañondo

[11] 3,993,079
[45] Nov. 23, 1976

[54] DEVICE FOR PERCUTANEOUS PARACENTESIS, INJECTION, DRAINAGE AND CATHETERIZATION

[76] Inventor: Carlos Alberto Henriques de Gatztañondo, Torre 17, Barcelona, Spain

[22] Filed: Nov. 28, 1975

[21] Appl. No.: 636,214

[30] Foreign Application Priority Data
Dec. 14, 1974 Spain .................................. 208409

[52] U.S. Cl. .............................. 128/347; 128/214.4
[51] Int. Cl.² ......................................... A61B 17/34
[58] Field of Search ................ 128/347, 348, 349 R, 128/215, 214.4, 221

[56] References Cited
UNITED STATES PATENTS

| | | |
|---|---|---|
| 1,248,492 | 12/1917 | Hill ...................................... 128/347 |
| 3,007,471 | 11/1961 | McClure, Jr. .................... 128/347 X |
| 3,500,828 | 3/1970 | Podhora ........................... 128/214.4 |
| 3,540,447 | 11/1970 | Howe .............................. 128/347 X |
| 3,893,445 | 7/1975 | Hofsess ........................... 128/221 X |

*Primary Examiner*—John D. Yasko

[57] ABSTRACT

A device for percutaneous paracentesis, injection, drainage and catheterization comprising a hypodermic needle having means for attachment to a syringe, with a central body portion having a reference mark and a smaller diameter leading end portion extending therefrom, its end terminating in a cutting bevel and a trocar adapted to surround the central body portion of the needle and capable of sliding thereon using it as a guide, having a graduated scale related to the overall length of the needle and having its end also terminating in a cutting bevel.

4 Claims, 6 Drawing Figures

U.S. Patent  Nov. 23, 1976  3,993,079
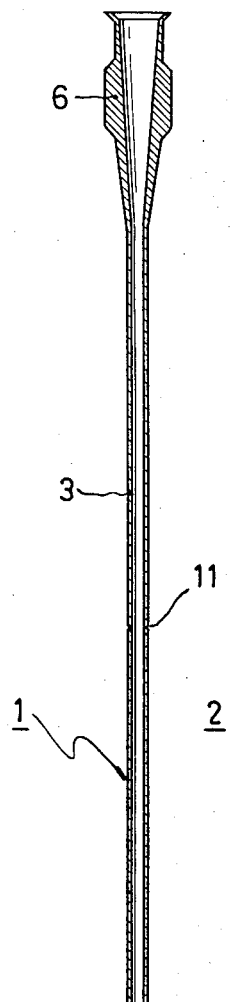
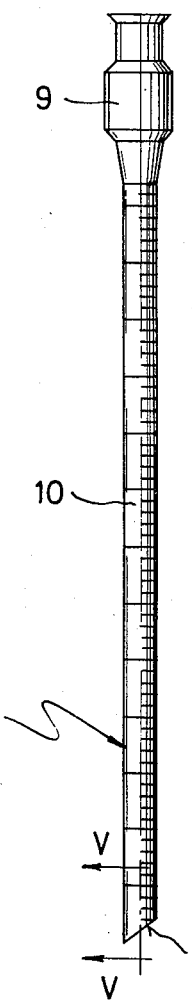
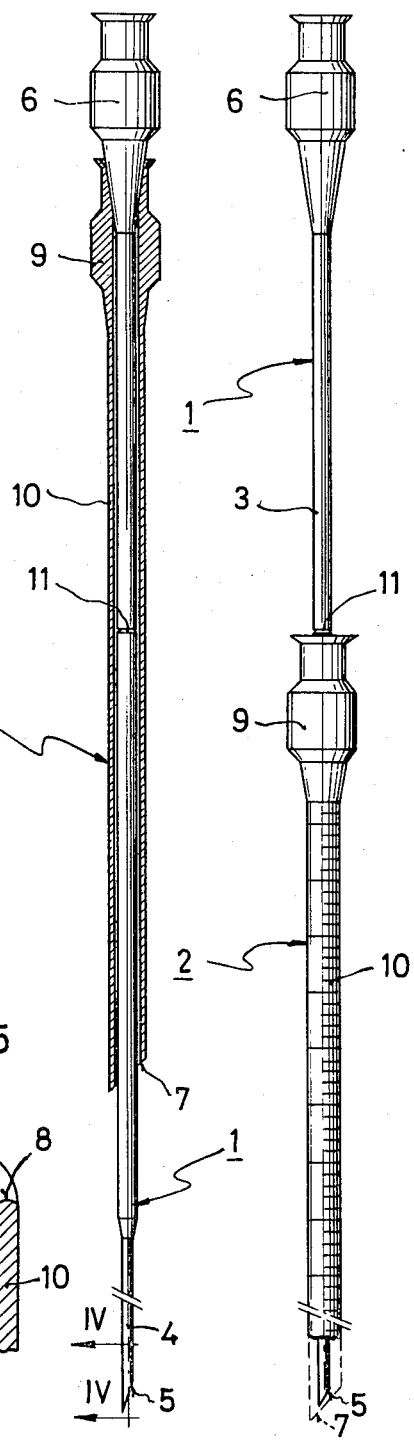
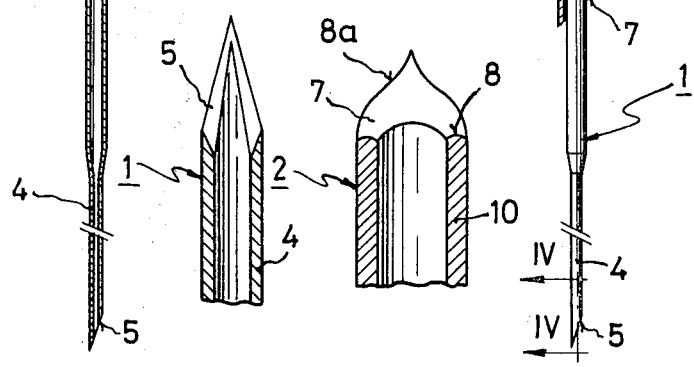

DEVICE FOR PERCUTANEOUS PARACENTESIS, INJECTION, DRAINAGE AND CATHETERIZATION

FIELD OF THE INVENTION

The present invention relates to a device for percutaneous paracentesis, injection, drainage and catheterization, of the type comprising a hypodermic needle having a connecting portion at one or trailing end for facilitating its attachment to a syringe and for insertion in blood vessels, lymph vessels and other organs. This device has been designed to overcome the disadvantages of known instruments used in the ordinary course of the way for the same functions and particularly to eliminate all traumatic movement that could damage delicate structures adjacent the operated area, as well as to obtain clear, safe access to the vessels or organs.

Outstanding applications of the present device are percutaneous catheterization of any deep artery or vein, central venous pressure evaluations, arteriographies of any organ, arterial catheterization for dialysis in renal block patients, parenteral hypernutrition with highly osmotic sera, selective arteriographies, cystographies, renal paracentesis for tumours, pyelographies by elimination in affections of the excretory systems with excluded kidney, nephrostomies by paracentesis, direct chemotherapy of deep tumours, paracentesis and catheterization of lymph vessels, foetal and placenta transfusions, percutaneous cholecystographies, drainage of purulent effused fluids, haemorrhages and many other applications.

SUMMARY OF THE INVENTION

The device of the invention is characterised in that said hypodermic needle comprises a central body portion extending from said connecting portion and having a reference mark, a leading end portion serving as continuation of said central body portion, said leading end portion being of smaller diameter than said central body portion and terminating in a sharp cutting bevel and in that it comprises a trocar being slightly shorter in length than said needle central body portion and having an internal diameter slightly larger than the external diameter of said central body portion, and having a connecting portion at one or trailing end adapted for connection to said connecting portion of said needle and being terminated at its other or leading end in a bevel which is not so sharp as said needle bevel, and having an external cutting edge and an internal blunt edge, and having also a graduated scale rising in value from said leading end towards said trailing end and, said scale being related to the total length of said needle, so that said needle is inserted in said trocar with the latter situated around said needle central body portion, which position is appropiate for starting use. In use the trocar moves lengthwise towards the leading end of said needle, so that when the leading ends of said needle and said trocar are mutually aligned, said reference mark on said needle central body portion is located at the level of the rear edge of said trocar.

In a preferred embodiment of the invention, the needle and trocar connecting portions are standardised to provide for attachment to conventional syringes.

In a further embodiment of the invention, the needle and trocar connecting portions are threaded and may be fitted with ears to facilitate their manipulation.

BRIEF DESCRIPTION OF THE DRAWINGS

Further objects and features of the invention will be disclosed in detail in the following description taken in conjunction with the accompanying drawings in which:

FIG. 1 is a paracentesis needle according to the invention;

FIG. 2 is a trocar for catheterization according to the invention;

FIG. 3 shows the needle and trocar of the previous Figures assembled together for joint use;

FIG. 4 is a detail in cross section of the leading end of the needle, along the plane of the line IV—IV of FIG. 3 and on an enlarged scale;

FIG. 5 is a detail in cross section of the other end of the trocar along the plane of the line V—V of FIG. 2 and on an enlarged scale; and FIG. 6 shows the relative positions of the trocar and needle on performing paracentesis, this being shown by the needle reference mark.

DETAILED DESCRIPTION OF THE INVENTION

The present device comprises essentially a hypodermic needle 1 and a trocar 2 made from stainless steel or any other appropriate material.

The needle 1 comprises a central body portion 3 having a portion 4 of lesser diameter as continuation and terminating in an sharp cutting bevel 5. The trailing end of the central body portion 3 has a connecting portion 6 for attachment to a syringe.

The trocar 2 is a tubular member slightly shorter in length than the central body portion 3 of the needle 1 and having an internal diameter slightly greater than the external diameter of said central body portion 3, its leading end terminating in a bevel 7 which is not so sharp as that of the needle 1 and having an external cutting edge 8a and an internal blunt edge 8. The trailing end of the trocar 2 has a conntecting portion 9 providing for attachment to the connecting portion 6 of the needle 1. The body portion 10 of the trocar 2 carries a graduated scale disposed on the side wall opposed to the tip of the bevel 7 to facilitate reading of the scale when operating and avoiding dangerous rotational movements. Said graduated scale increases from a minimum reading at the leading end to the trailing end and is related to the overall length of the needle 1.

In a preferred embodiment, the overall length of the needle 1 is 12 cms, with the central body portion 3 measuring 8.5 cms long by 1.4 mm diameter, while the front portion 4 is 0.8 mm diameter. In turn, the trocar is 8 cms long and has an internal diameter of 1.6 mm, although these dimensions may vary according to the needs of the vessels and regions to be subjected to paracentesis, visualization or catheterization.

The connecting portions 6 and 9 of the needle 1 and trocar 2 are provided for adaptation to all universal and American syringe pitches. They may also be threaded and have lugs or wings for manipulation.

The bevelled end 5 of the needle 1 is extremely sharp, whereas the bevelled end 7 of the trocar has an internal blunt portion 8 to avoid the risk of severing a blood vessel or even a lymph vessel.

It is contemplated that the needle 1 should carry a mark 11 which is useful as a reference, when performing paracentesis, of the position of the trocar 2 with respect to the needle 1, in other words, when the leading ends 5 and 7 are aligned one with the other, the rear edge of the trocar 2 is located at the level of the mark 11, as seen in FIG. 6.

The device of the invention is used as follows. The needle 1 is inserted inside the trocar 2, with the latter mounted around the central body portion 3 of the needle 1. It is then attached to a syringe containing an anaesthetic, whereby the first function of the needle is fulfilled, by puncturing the chosen part of the body so as to inject the anaesthetic therein. Subsequently, the second function of the needle 1 is performed, consisting of locating the desired vessel or organ by paracentesis. Once the above objective is attained, the location and depth of said vessel or organ is known by way of the graduated scale of the trocar 2. Finally, the third function of the needle is fulfilled. This consists of guiding the trocar 2 for deep penetration in the vessel or organ while avoiding the risk of any traumatic movement which could damage delicate neighboring structures. This operation allows for subsequent catheterization or visualization. A look at the mark 11 at the level of the rear edge of the trocar 2 shows when the respective leading ends 5 and 7 are aligned one with the other.

What I claim is:

1. A device for percutaneous paracentesis, injection, drainage and catheterization, of the type comprising a hypodermic needle having a connecting portion at one end for attachment to a syringe, wherein said hypodermic needle has a central body portion extending from said connecting portion and having a reference mark, a leading end portion serving as continuation of said central body portion, said leading end portion being of smaller diameter than said central body portion and terminating in a sharp cutting bevel and surrounded by a trocar being slightly shorter in length than said needle central body portion and having an internal diameter slightly larger than the external diameter of said central body portion and having a connecting portion at one end for attachment to said connecting portion of said needle and being terminated at its other or leading end in a bevel which is not as sharp as said needle bevelled end, and having an external cutting edge and an internal blunt edge, and having a graduated scale rising in value from said leading end towards said one end, said scale being related to the total length of said needle, so that when said needle is inserted in said trocar, with the latter mounted around said needle central body portion, the trocar is movable lengthwise toward the leading end of said needle, so that when the leading ends of said needle and said trocar are mutually aligned, said reference mark on said needle central body portion is located at the level of the rear edge of the trocar.

2. The device of claim 1, wherein the connecting portions of said needle and said trocar are standardized for attachment to conventional syringe pitches.

3. The device of claim 1, wherein the connecting portions of said needle and said trocar are threaded.

4. The device of claim 1, wherein the connecting portions of said needle and said trocar have lugs or wings for facilitating their handling.

* * * * *